US012649045B2

(12) United States Patent
Paesano-Lima et al.

(10) Patent No.: US 12,649,045 B2
(45) Date of Patent: Jun. 9, 2026

(54) LOCKING STABILIZER FOR CATHETER

(71) Applicant: Tufts Medical Center, Inc., Boston, MA (US)

(72) Inventors: Lori Ann Paesano-Lima, Saugus, MA (US); Kevin M. Small, North Andover, MA (US)

(73) Assignee: Tufts Medical Center, Inc., Boston, MA (US)

( * ) Notice: Subject to any disclaimer, the term of this patent is extended or adjusted under 35 U.S.C. 154(b) by 825 days.

(21) Appl. No.: 17/963,520

(22) Filed: Oct. 11, 2022

(65) Prior Publication Data

US 2024/0115834 A1     Apr. 11, 2024

(51) Int. Cl.
   *A61M 25/01*     (2006.01)
   *A61M 25/02*     (2006.01)

(52) U.S. Cl.
   CPC ....... *A61M 25/01* (2013.01); *A61M 2025/024* (2013.01)

(58) Field of Classification Search
   CPC .............. A61M 25/01; A61M 25/0111; A61M 25/0113; A61M 25/02; A61M 2025/0206; A61M 2025/0213; A61M 2025/0246; A61M 2025/0253; A61M 2025/0266; A61M 2025/0273; A61M 2025/028; A61M 2025/0293; A61M 2025/024; A61M 2025/0233; A61M 2039/0229; A61M 2039/0279; A61F 5/448
   See application file for complete search history.

(56) References Cited

U.S. PATENT DOCUMENTS

| | | | |
|---|---|---|---|
| 4,170,995 A | 10/1979 | Levine et al. | |
| 2005/0096688 A1 | 5/2005 | Slazas et al. | |
| 2008/0183154 A1 | 7/2008 | Racz et al. | |
| 2011/0118670 A1 | 5/2011 | Kay et al. | |
| 2020/0238052 A1* | 7/2020 | Stephan | A61M 39/0247 |
| 2022/0062590 A1* | 3/2022 | Berth | A61M 25/02 |
| 2022/0126066 A1* | 4/2022 | Clayman | A61M 25/0017 |

OTHER PUBLICATIONS

International Search Report and Written Opinion issued in PCT/US2023/034517, mailed Jan. 17, 2024 (16 pages).

* cited by examiner

*Primary Examiner* — Laura A Bouchelle
*Assistant Examiner* — Marissa Taylor
(74) *Attorney, Agent, or Firm* — Young Basile Hanlon & MacFarlane, P.C.

(57) ABSTRACT

A locking stabilizer for inhibiting movement of an indwelling catheter includes an actuator having an actuator opening for receiving the catheter into the stabilizer, a base having a base opening through which the catheter exits the locking stabilizer, and a torque-actuated gripper between the cover and the base. The torque-actuated gripper exerts exert a variable gripping force on a section of the catheter, the section extending between the base and the cover. The actuator is operable to cause the grip to transition between exerting the gripping force and releasing the gripping force.

15 Claims, 8 Drawing Sheets

LOCKING STABILIZER FOR CATHETER

BACKGROUND OF THE INVENTION

This disclosure relates to medical devices and in particular to stabilizing a catheter through which fluid transfer takes place for an extended period, such as for more than twenty-four hours.

There exist a variety of conditions in accumulated fluids require drainage from the body or in which a fluid is to be infused into the body. In both cases, such fluid transfer is often carried out using an indwelling catheter.

An indwelling catheter, whether it is used for drainage or infusion, is vulnerable to mechanical disturbances that cause movement thereof. Movement of this catheter contributes to patient discomfort. In some cases, movement is sufficient to cause the catheter to fall out altogether.

SUMMARY OF THE INVENTION

The invention provides a locking stabilizer to reduce the risk of inadvertent displacement of an indwelling catheter and to do so without directly contacting the contacting the wound through which the catheter extends.

In one aspect, the invention features a locking stabilizer for inhibiting movement of an indwelling catheter. Such a stabilizer includes an actuator having an actuator opening for receiving the catheter into the locking stabilizer, a base having a base opening through which the catheter exits the locking stabilizer, and a gripper between the cover and the base. The gripper is configured to exert a variable gripping force on that section of the catheter that extends between the base and the cover. The actuator is operable to cause the grip to transition between exerting the gripping force and releasing the gripping force.

Embodiments include those in which the gripper includes filaments that extend between the actuator and the base. In such embodiments, each of the filaments forms an angle relative to the actuator. This angle transitions between a first value, in which the gripper exerts the gripping force on the catheter, and a second value, in which the gripper releases the gripping force from the catheter.

Further embodiments include those in which the gripper is configured to be twisted by the actuator so as to exert the gripping force on the catheter and to be untwisted by the actuator to release the gripping force from the catheter.

In still other embodiments, the gripper includes filaments that extend between the actuator and the base. In these embodiments, each filament transitions between extending along a helical path for gripping the catheter and extending along a straight path for releasing the catheter.

Also among the embodiments are those in which the gripper extends along a long path to exert the gripping force on the catheter and a short path, which is shorter than the long path, to release the gripping force from the catheter.

In some embodiments, the gripper includes a resilient tube that transitions between a first state, in which the tube exerts the gripping force on the catheter, and a second state, in which the tube releases the gripping force from the catheter. In such embodiments, the actuator causes the tube to transition into the first state.

Since catheters come in different sizes, it is useful to also have embodiments in which the actuator opening is one of several actuator openings of different sizes, each of which corresponds to a different size of catheter.

In some embodiments, the actuator is transparent to light.

In other embodiments, the locking stabilizer further includes a lock that causes the gripping force to be maintained on the catheter. Among these are embodiments in which the lock includes a gear and a lock ring, in which case the actuator is coupled to the gear to engage the lock ring and the extent to which one rotates the gear controls a gripping force on the catheter. Also among these are those embodiments in which the locking stabilizer further includes a lock ring having a latch. In these embodiments, exerting a force on the latch causes the gripper to release the catheter.

Still other embodiments include those in which base includes an adhesive layer and a release layer that, when peeled off, exposes the adhesive layer, thereby enabling the locking stabilizer to adhere to a skin barrier that isolates the locking stabilizer from direct skin contact with a patient who receives the catheter.

Yet other embodiments include, in addition to the locking device itself, a skin barrier through which the catheter extends. The skin barrier includes an inner face that faces skin of a patient and an outer face that faces away from the skin. The locking stabilizer is disposed on the outer face of the skin barrier. Examples of suitable skin barriers include wound dressings and bags, such as ostomy bags.

In another aspect, the invention includes placing a locking stabilizer on a skin barrier that is disposed over an entry point into a patient, inserting the catheter through the locking stabilizer and into the entry point, and causing the locking stabilizer to exert a radially inward force to secure the catheter.

In some practices, causing the locking stabilizer to exert the radially inward force includes causing torsion in a gripper that surrounds a portion of the catheter that is within the locking stabilizer.

In other practices, causing the locking stabilizer to exert the radially inward force includes twisting an actuator on the locking stabilizer, wherein twisting the actuator causes the locking stabilizer to exert a radially inward force that secures a section of the catheter that is within the locking stabilizer.

In some cases, the catheter has a first size, and the locking stabilizer is configured to accommodate a catheter that has second size that differs from the first size. Such practices include an additional step of causing the locking stabilizer to discontinue accommodating a catheter of the second size and to begin accommodating a catheter of the first size.

Other practices those in which placing the locking stabilizer on the skin barrier includes placing the locking stabilizer on the skin barrier and either clipping the locking stabilizer to the skin barrier, such as clipping the locking stabilizer to an ostomy bag and those in which placing the locking stabilizer on the skin barrier includes causing the locking stabilizer to stick to the skin barrier, for example by peeling a release layer to expose an adhesive and using the adhesive to stick the locking stabilizer and a skin barrier, such as a dressing, together.

Other features and advantages of the invention are apparent from the following description, and from the claims.

DETAILED DESCRIPTION

Figure 1:
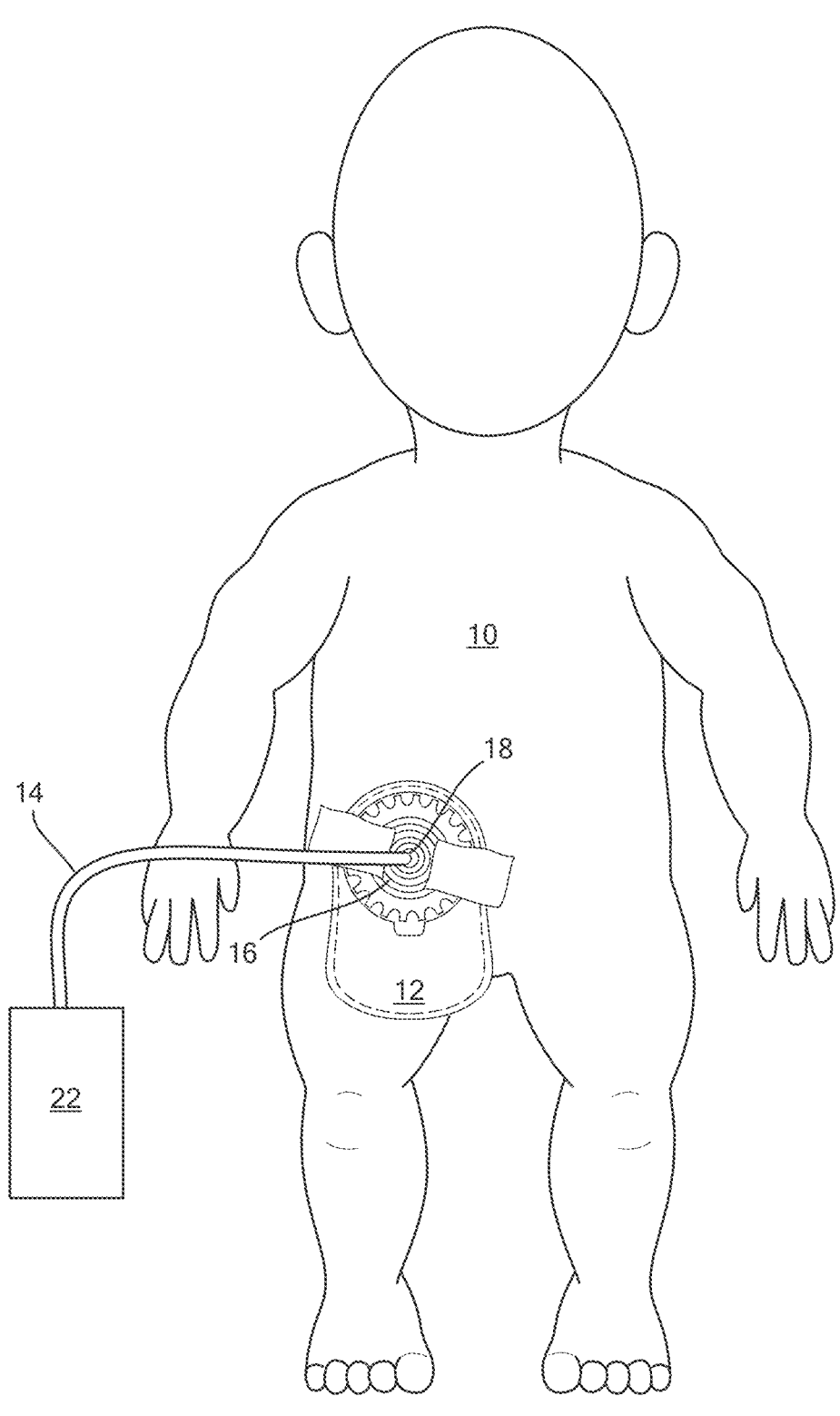
FIG. 1 shows a locking stabilizer in use with a skin barrier on a patient.

FIG. 1 shows a patient 10 after having undergone a procedure that requires an extended period of fluid transfer using an indwelling catheter. The direction of fluid transfer is either away from patient 10, in which case it is referred to as "drainage," or towards the patient 10, in which case it is referred to as "infusion."

A skin barrier 12 coupled to the patient 10 covers an entry point into which a catheter 14 is inserted. This entry point is typically a wound in the patient. The catheter 14 passes through a locking stabilizer 16 mounted to the skin barrier 12. As a result, the locking stabilizer 16 stabilizes the catheter 14 without having to contact the entry point into which the catheter 14 is to be inserted.

Figure 2:
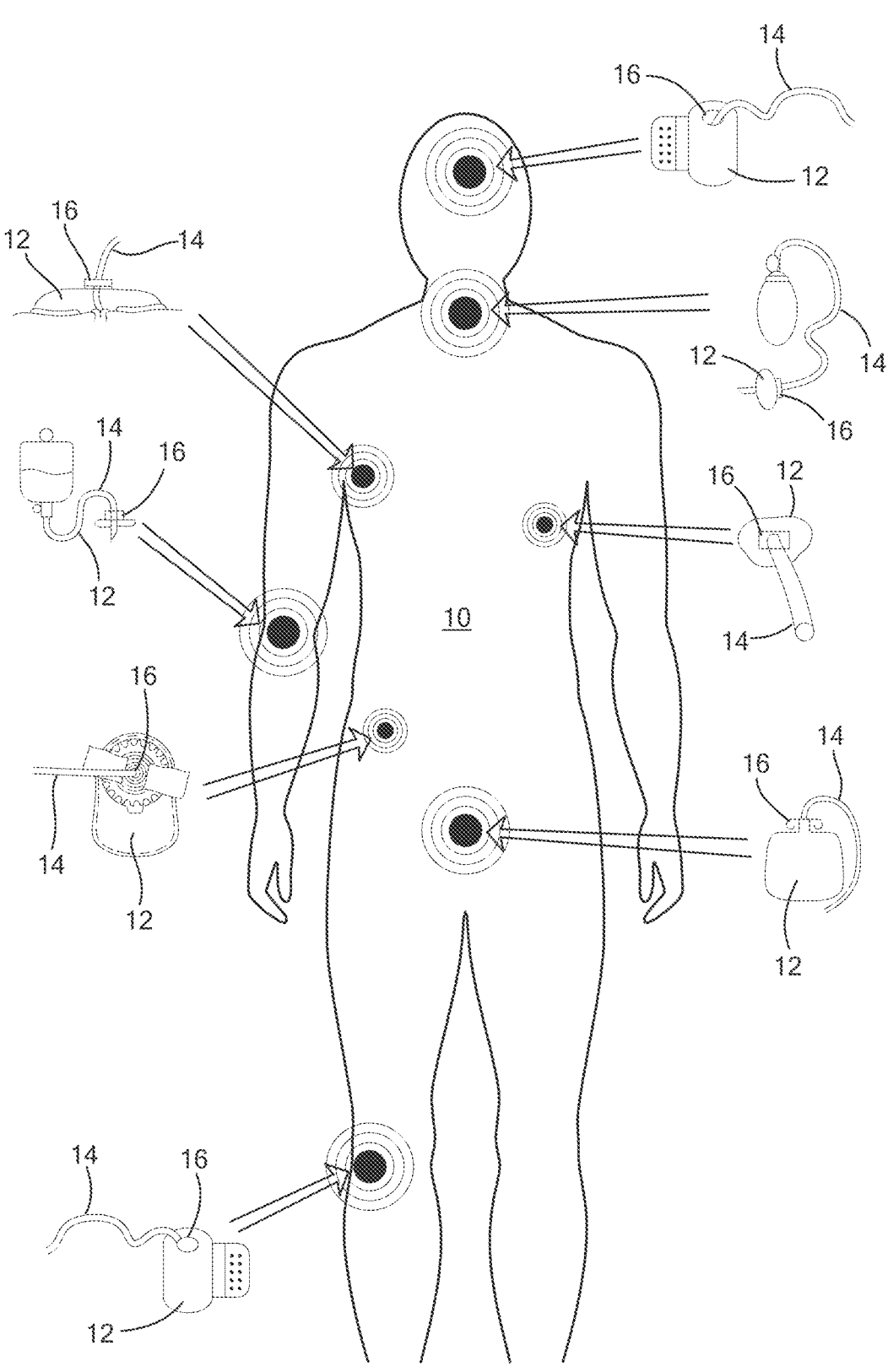
FIG. 2 shows various skin barriers and sites at which the locking stabilizer of FIG. 1 can be used.

FIG. 2 shows different kinds of catheters 14 and skin barriers 12 with which the locking stabilizer 16 can be used to stabilize the catheter 14. Examples include a pericardial catheter or chest tube used in connection with a variety of cardiac conditions, an intravenous line, an indwelling catheter following prostate surgery, a catheter that is used to drain fluid arising as a result of, for example, certain types of cancer, as in a catheter used in connection with a Jackson-Pratt drain. Further examples include a central venous catheter, a catheter used for surgical infusion, a catheter used for surgical drainage such as following a mastectomy, a Foley catheter, a urinary catheter that is used in connection with certain urological conditions, and/or a catheter that is used in connection with otorhinolaryngological drainage, ventriculostomy drainage, and joint aspiration.

In the illustrated embodiment, the skin barrier 12 is a bag that stores drained fluid for later disposal. Examples of such a skin barrier 12 include an ostomy bag, such as a colostomy, ileostomy, or urostomy bag. Such bags are typically made of a breathable material that has been attached to the skin using a medical-grade adhesive. Other examples of a skin barrier 12 that takes the form of a bag include a stoma bag, which fits around a stoma and adheres to the abdomen using a flange.

Depending on the nature of the procedure, other types of skin barrier 12 are used.

For example, in some cases, the skin barrier 12 takes the form of a dressing to which the locking stabilizer 16 adheres using an adhesive that is exposed upon removal of a release layer. Examples of suitable dressings that can function as the skin barrier 12 include gauze, transparent film dressings, foam dressings, hydro-conductive dressings, and antimicrobial or antibacterial dressings. Other examples include anchor pads, composite dressings, absorptive dressings, hydrogel dressings, and hydrocolloid dressings.

The locking stabilizer 16 remains above the barrier 12 and thus isolated from the skin by the skin barrier 12. The locking stabilizer 16 thus provides a way to easily and effectively urge a catheter 14 to remain in place without the need to actually contact the patient's skin. In some embodiments, the dressing that isolates the locking stabilizer 16 from the skin is itself clear and thus provides the clinician with a way to inspect the wound and the catheter's placement therein.

For ease of exposition, the locking stabilizer 16 will be described in the context of its use following an ostomy procedure. The structure and operation of the locking stabilizer 16 is, however, agnostic to the nature of the skin barrier 12.

Figure 3:
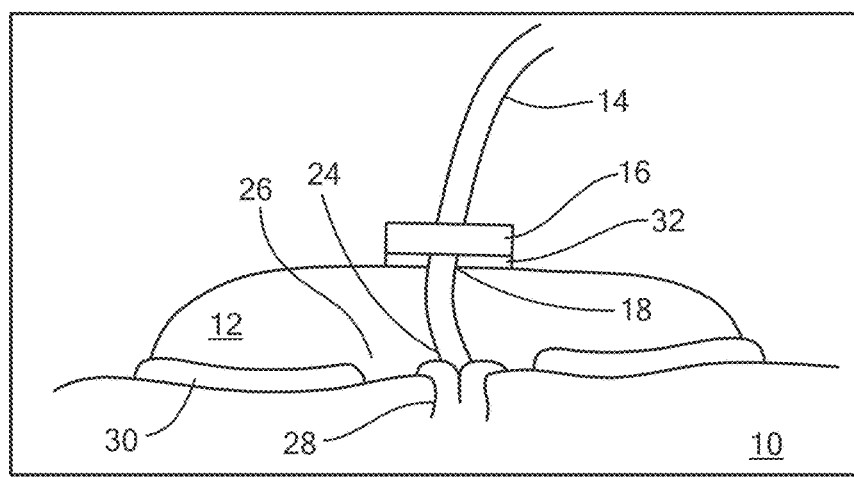
FIG. 3 shows a cross-section of a skin barrier in the form of the ostomy bag shown in FIG. 2 and having the locking stabilizer deployed thereon.

FIG. 3 shows what becomes of the catheter 14 once it passes through the skin barrier 12. In this embodiment, in which the barrier 12 is a bag, there exists a front opening 18 through which the catheter 14 passes into the bag 12 and a rear opening 26 through which the catheter's distal end 24 passes into a fistula 28.

FIG. 3 also shows first and second dressings 30, 32 that are used in conjunction with the skin barrier 12. The first dressing 30 surrounds the rear opening 26 and couples the skin barrier 12 to the patient 10. The second dressing 32 surrounds the front opening 18 and couples the skin barrier 12 to the locking stabilizer 16. In a typical embodiment, the first and second dressings 30, 32 are adhesive on both sides.

Figure 4:
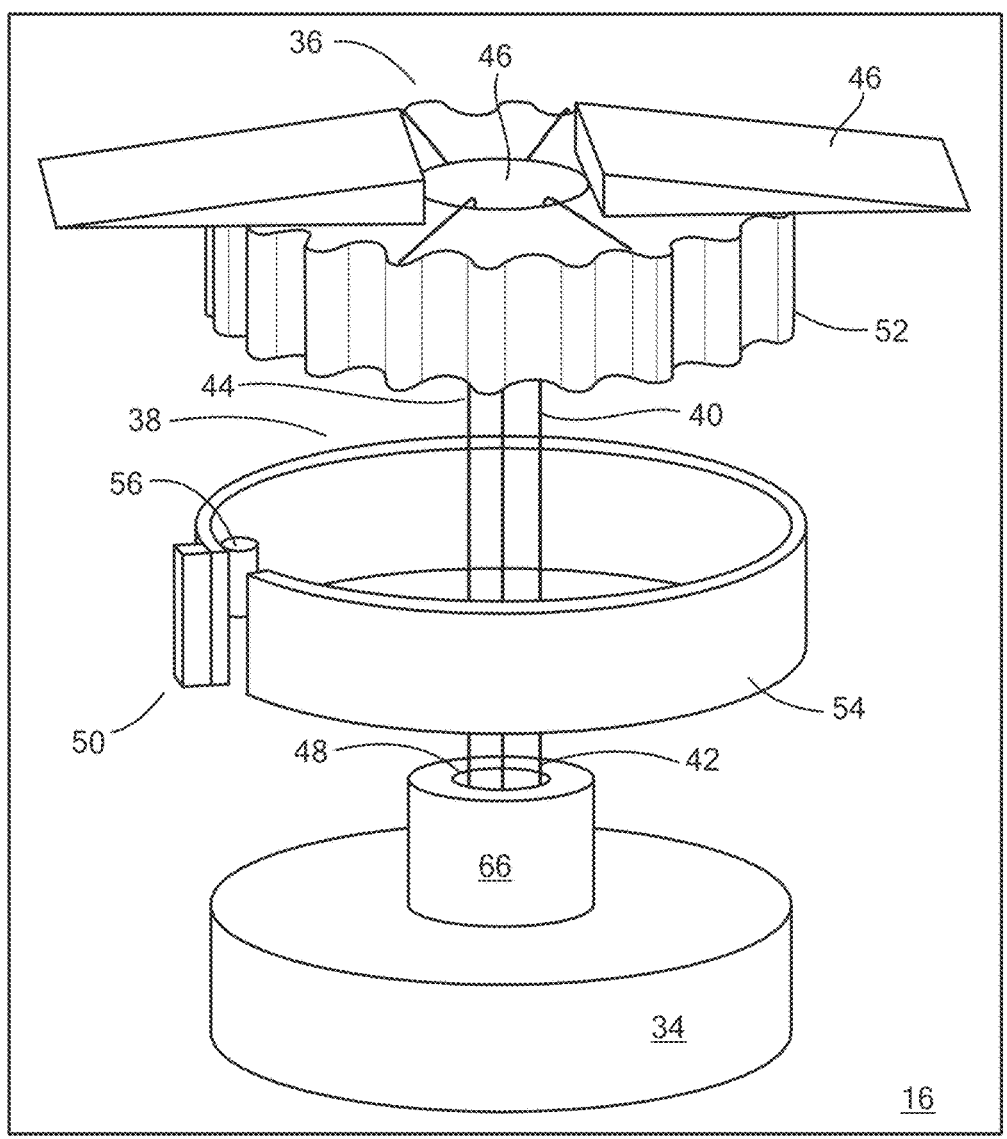
FIG. 4 is an exploded view of the locking stabilizer shown in FIG. 1.

As shown in FIG. 4, the locking stabilizer 16 comprises a base 34. An actuator 36 disposed above the base 34 covers the locking stabilizer 16. Suitable materials for use in the base 34 and the actuator 36 include silicone with polyurethane.

The base 34 is joined to the skin barrier 12 at the second dressing 32. Attachment is thus easily carried out by a peel-and-stick operation in which a release layer is peeled off the base 34 and/or the second dressing 32 to expose an adhesive. To further reduce risk of infection, it is useful to coat the bottom of the base 34 with an adhesive having anti-microbial properties.

Figure 5:
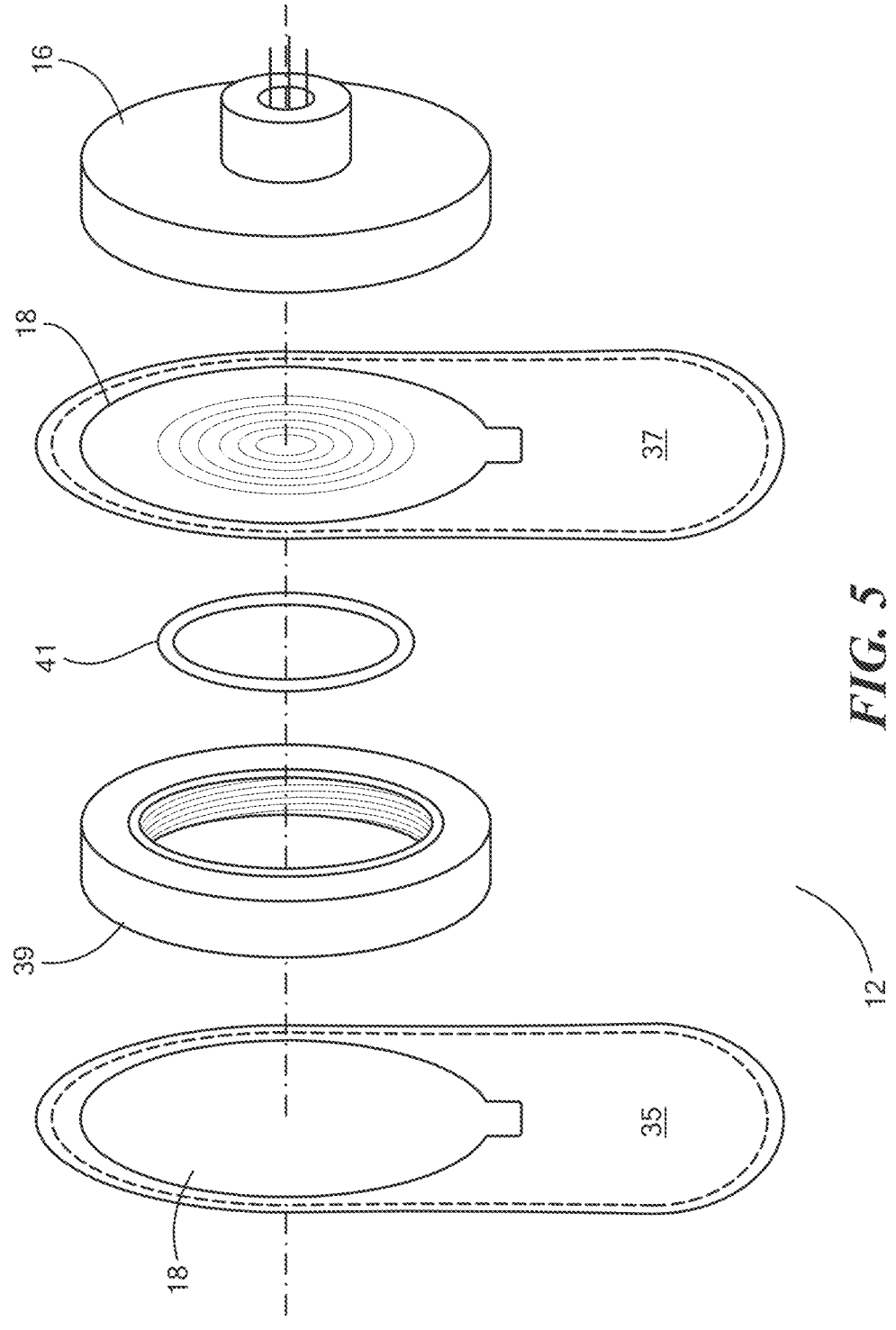
FIG. 5 shows an alternative coupling in which the locking stabilizer of FIG. 1 engages a flange.

FIG. 5 shows a particular embodiment in which the skin barrier 12 includes inner and outer faces 35, 37 that defines a volume therebetween. The inner face 35 faces and contacts the patient 10. The outer face 37 faces away from the patient 10. This is a typical configuration when the skin barrier 12 is an ostomy bag that holds fluid within that volume. In this embodiment, the base 34 engages a flange 39 that through the opening 18 in the outer face 37. An O-ring 41 within the flange 39 ensures a fluid-tight seal to suppress leakage from the volume. In some embodiments, the base 34 clips onto the flange 39. In other embodiments, the flange 39 is threaded and the base 34 screws onto the flange 39.

In some embodiments, the locking stabilizer's base 34 has a polygonal cross-section. A polygon with many sides tends to promote a better grip with interlocking components to be described below. In a preferred embodiment, the polygon has approximately twenty sides.

The second dressing 32 is preferably a hypoallergenic, breathable, and lightweight dressing 32 that remains in place. Such a dressing 32 is comfortable, resilient, easy to apply, and lasts for an extended period, for example on the order of a week, before needing to be changed. Once the locking stabilizer 16 has been secured in place, it is preferable to cover it with a waterproof over-dressing, or protective cover. This enables the patient 10 to carry out such daily activities as showering, bathing, and even swimming.

A gripper 38 extends between the base 34 and the actuator 36. In the illustrated embodiment, the gripper 38 comprises strands 40, or filaments, each of which comprises a bottom end 42 that is coupled to the base 34 and a top end 44 coupled to the actuator 36. Thus, in addition to its role of covering the locking stabilizer 16, the actuator 36 also actuates the gripper. It does so by transforming an applied torque into a radially-inward force that is sufficient to grip the catheter 14 but falls far short of that required to actually constrict the catheter 14.

The actuator 36 includes an actuator opening 46 that is aligned with a corresponding base opening 48 in the base 34. The diameters of the actuator opening 46 and the base opening 48 are selected to accommodate the diameter of the catheter 14. In operation, the catheter 14 passes through the actuator opening 46 and the base opening 48. As it does so, it passes between the strands 40 of the gripper 38.

Rotating the actuator 36 relative to the base 34 twists the strands 40. This twisting causes the strands 40 to move radially inward, thus coming into contact with the catheter 14. Continued twisting causes the strands 40 to exert a centripetal force against the catheter 14, thereby gripping the catheter 14 securely. This centripetal force is great enough to stabilize the catheter 14 so as to isolate it from mechanical disturbances. However, the centripetal force is not so great that it begins to actually squeeze the catheter 14 and prevent infusion therethrough.

The actuator 36 comprises a handle 46 having wings that extend radially outward along a diameter thereof. This handle 46 enables the clinician to easily rotate the actuator 36 clockwise or counter-clockwise to increase or decrease the centripetal force applied by the strands 40. Such control is important to ensure that the grip on the catheter 14 is no more than is required to secure the catheter 14 against movement in response to external forces of the type that would commonly be expected to arise while the catheter 14 is in use.

After the clinician has rotated the handle 46 by the desired amount, it is useful to enable the clinician to leave and do something else. After all, it would be inconvenient for a clinician to manually apply the relevant torque to the handle 46 for an extended period.

To achieve this, the locking stabilizer 16 further includes a lock 50 to maintain the handle's position. The lock 50 comprises a gear 52 attached to the actuator 36 and a retaining ring 54 disposed between the actuator 36 and the base 34. The retaining ring 54 includes a post 56 that engages the gear 52.

Figure 6:
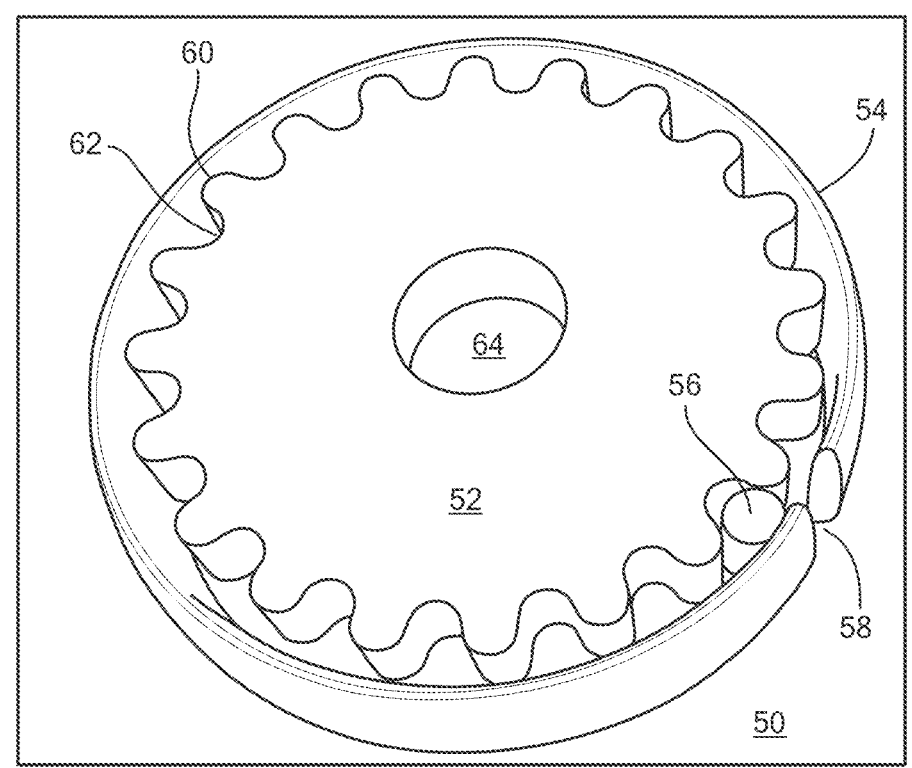
FIG. 6 shows a lock for maintaining the locking stabilizer shown in FIG. 1 at a particular position.

Referring now to FIG. 6, the retaining ring's post 56 is located adjacent to a discontinuity 58 in the retaining ring 54. As a result, the post 56 is free to move radially outward in response to a radially-outward force and to spring back in a radially-inward direction in response to removal of such a force.

In a preferred embodiment, the retaining ring 54 is a polygonal structure. Such a structure promotes binding of the gear 52 in a locked position. A suitable number of sides for such a polygonal structure is twenty-four.

The gear 52 comprises teeth 60 with interdental recesses 62 between adjacent teeth 60. At equilibrium, the post 56 settles within one of the interdental recesses 62, thus preventing rotation of the gear 52. When settled within an interdental recess 62, the post 56 locks the gripper 38 into a desired state. To change the gripper's state, the clinician uses the actuator 36 to turn the gear 52. Doing so causes the post 56 to climb up a tooth 60 and out of the interdental recess 62. Continued rotation allows the post 56 to settle into an adjacent interdental recess 62, thereby changing the state of the gripper 38. The number of interdental recesses 62 determines the number of states of the gripper 38.

In some embodiments, the gear 52 is a parametric gear that consists of twenty teeth 60 and that has an overall non-involute circular profile. A suitable implementation features a gear 52 having a zero-degree grade, a pitch of eight tenths of an inch, a height of seventy-nine hundredths of an inch, and a bore diameter of twenty-seven hundredths of an inch. The gear 52 serves as a main attachment point for the gripper 38 that will ultimately bind the catheter.

Figure 7:
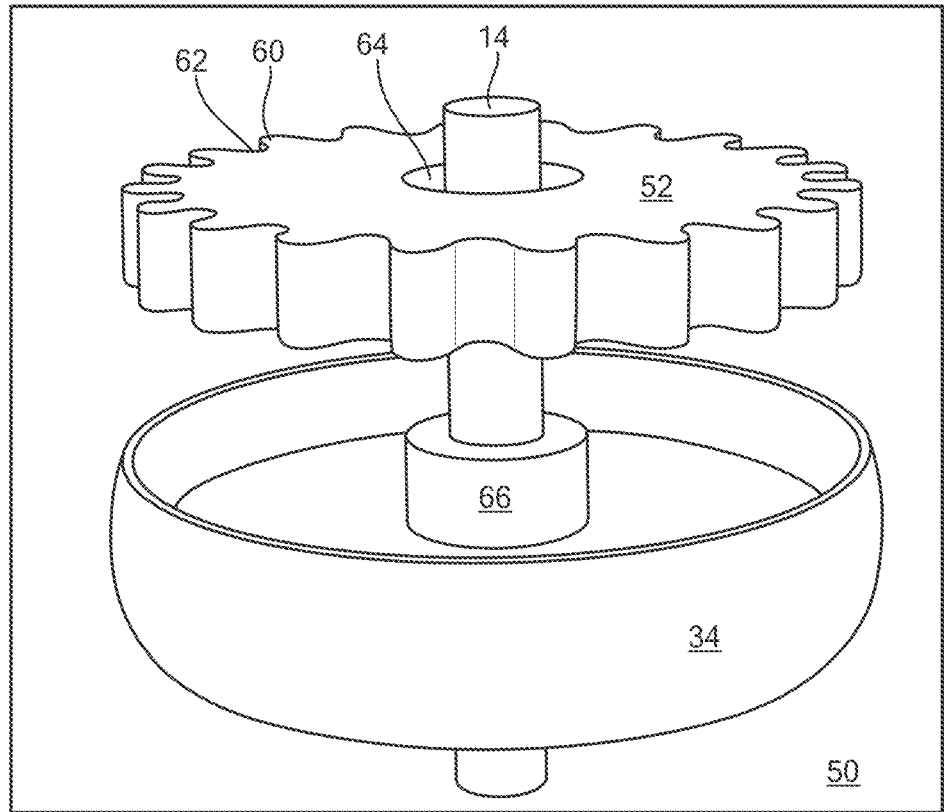
FIG. 7 shows an exploded view of a gear placed on a base of the locking stabilizer shown in FIG. 1 to form the lock shown in FIG. 4.
Figure 8:
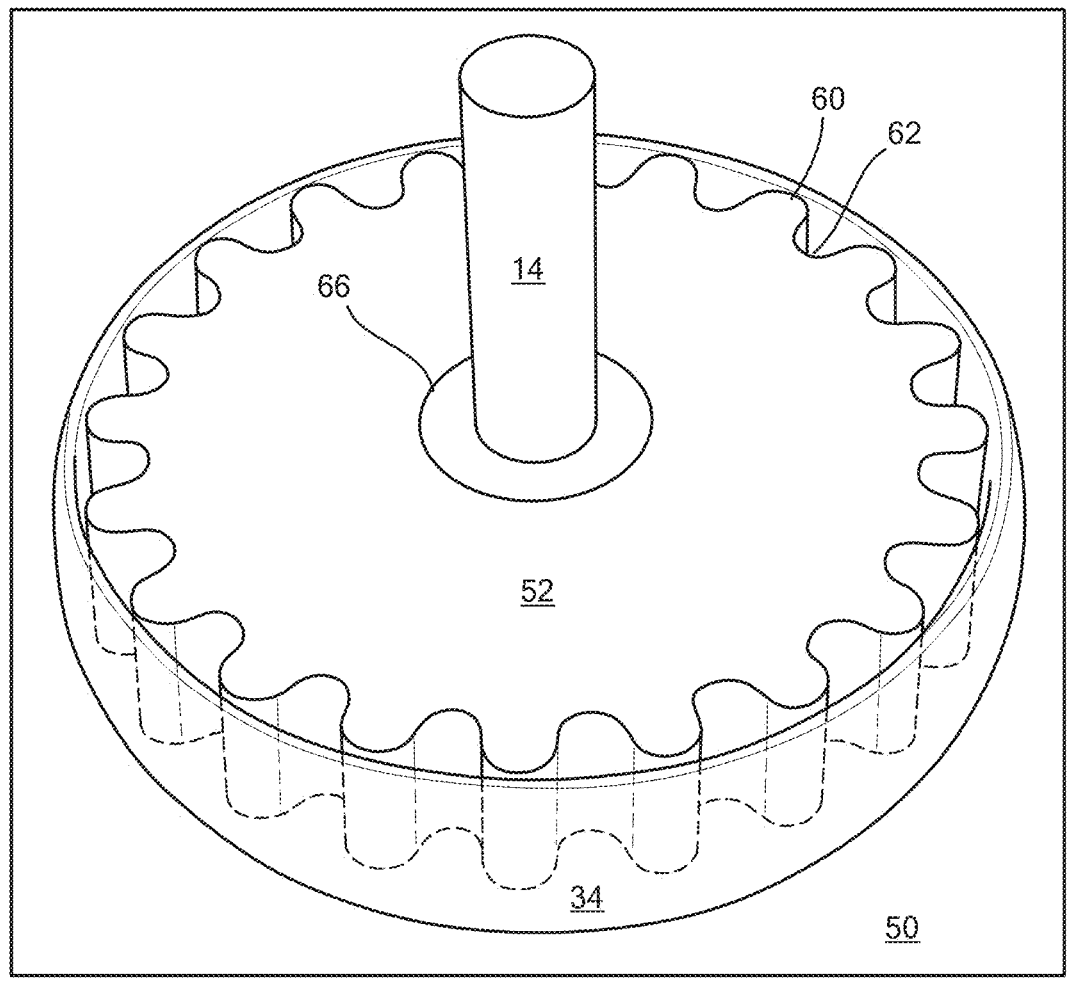
FIG. 8 shows an assembled view corresponding to FIG. 5.

As shown in the exploded view of FIG. 7 and in the corresponding assembled view of FIG. 8, the gear 52 includes a gear opening 64 that both provides passage for the catheter 14 and also engages an axle 66 that extends vertically upward from the base 34, as shown in FIG. 4. This results in a rotary joint about which the gear 52 rotates.

Figure 9:
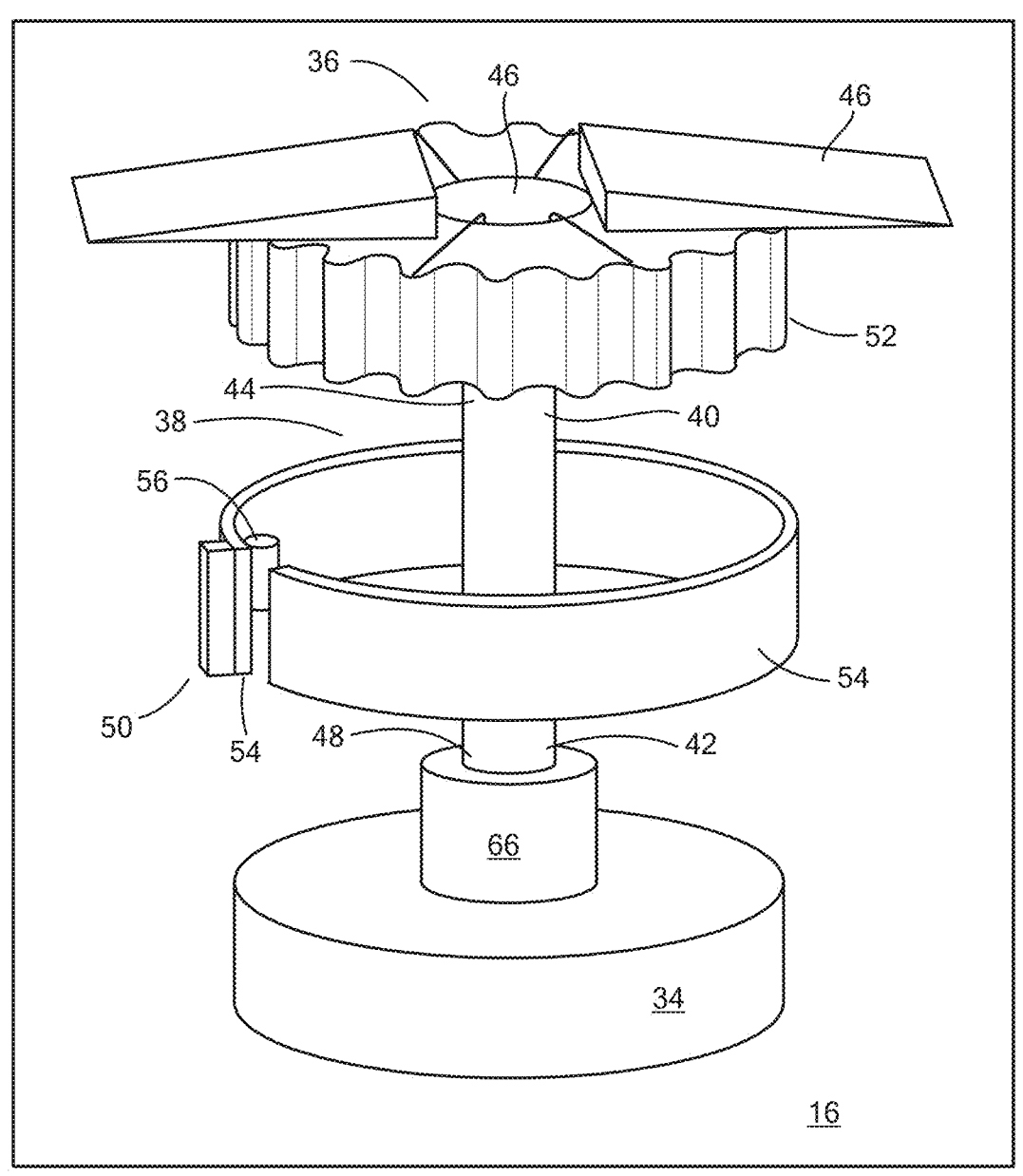
FIG. 9 is an alternative embodiment of the locking stabilizer shown in FIG. 3 but with a sleeve replacing the strands.
Figure 10:
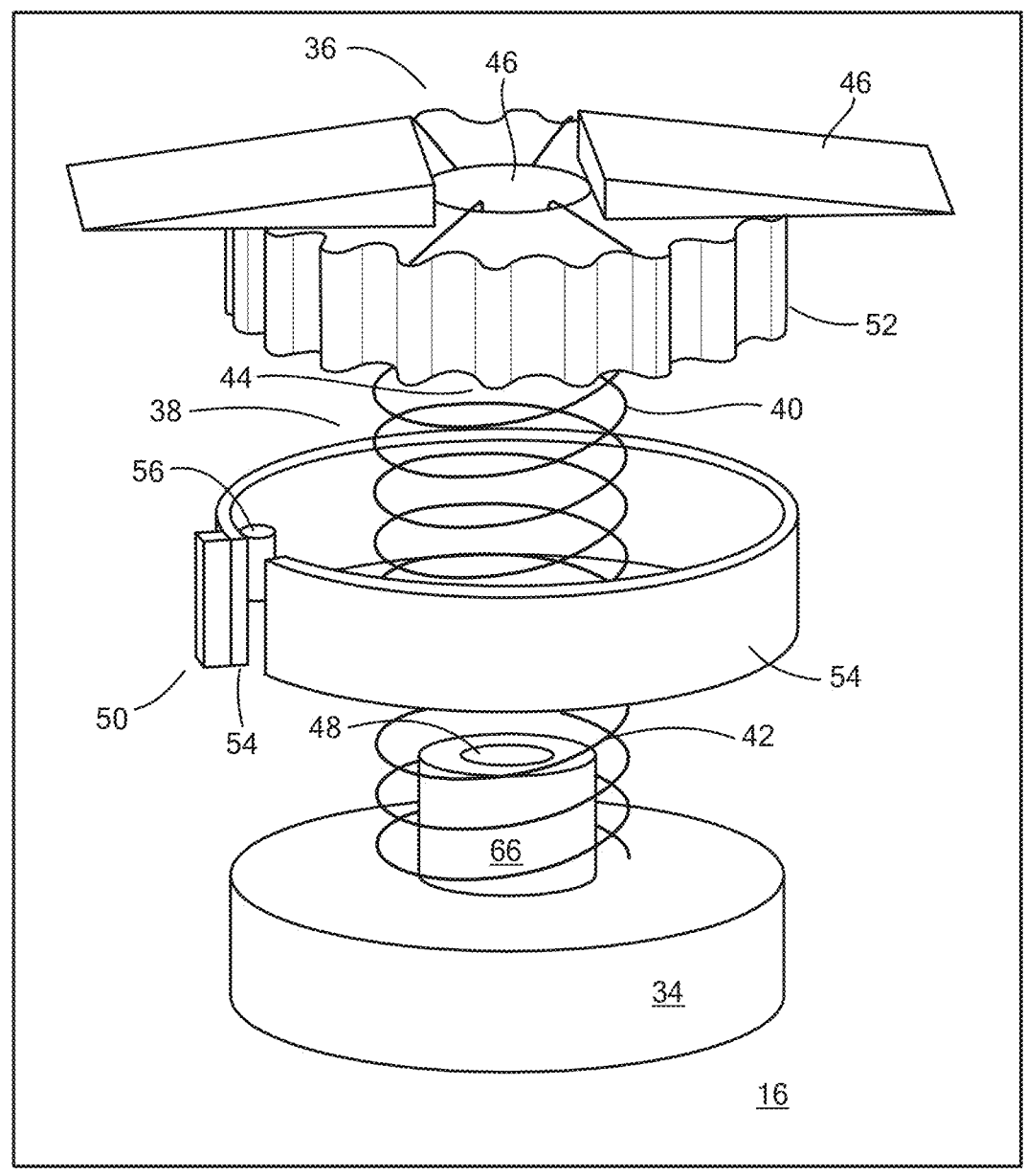
FIG. 10 is an alternative embodiment of the locking stabilizer shown in FIG. 3 but with a spring replacing the strands.

The illustrated embodiment, in which the gripper 38 is implemented by plural strands 40, is particularly useful for a catheter 14 having a small diameter. For a large catheter 14, it is useful to implement the gripper 38 by a sleeve or tube, as shown in FIG. 9. Suitable materials for the sleeve, tube, and filaments include a nitrile. Also among the embodiments are those in which the gripper 38 is implemented by a spring, as shown in FIG. 10.

A locking stabilizer 16 along the lines of the foregoing is usable for a variety of catheter sizes, including sizes ranging from 2 Fr to 24 Fr. Although described in the context of irrigating a mucosal fistula in an infant, the locking stabilizer's ability to stabilize a catheter 14 without actually contacting a wound is useful for stabilizing a catheter in other contexts. The locking stabilizer 16 is thus usable not only with neonatal patients, as described herein, but for infants, children, teenagers, and adults, both in a hospital and in a home-care setting. Its use is by no means restricted to humans. The locking stabilizer 16 is also applicable in a veterinary context for indwelling catheters 14 in small animals. The locking stabilizer 16 accommodates most brands of catheters 14 or plastic insertion tubes and can thus be used to secure passive and active drain tubes for post-operative recovery and healing of wounds.

In some embodiments, the actuator 36 is transparent. A transparent actuator 36 provides a way to see the catheter 14 during insertion thereof and to assess the condition of the skin around the wound.

In other embodiments, the actuator 36 comprises a dial that is rotatable to accommodate different sizes of catheters 14.

In some cases, it is necessary to remove the locking stabilizer 16. To accommodate this feature, it is useful for the locking stabilizer 16 to include a release that is attached to the side of the base 34 for quick removal.

The locking stabilizer 16 can be attached to many products, such as a skin barrier 12. In some embodiments, attachment is carried out by peeling a release layer off an adhesive layer and sticking the exposed adhesive layer to the bag's outer surface. In either embodiments, attachment is carried out by clipping the locking stabilizer 16 to the skin barrier 12 using a flange-style clip. In either case, doing so stabilizes the in-dwelling catheter 14 for infusing fluid, as is carried for re-feeding the mucus fistula of a neonate during post-operative recovery from a colostomy and also for draining fluid during post-surgical recovery and healing. Regardless of whether it has been attached by adhesion or by mechanical means, such as by a clip, the locking stabilizer 16 also helps prevent tugging of an indwelling catheter 14 at a wound site, thereby reducing patient discomfort and risk of infection. In addition, the locking stabilizer 16 suppresses the tendency of an indwelling catheter to be displaced by the patient's movement.

As described above, embodiments of the approach include an apparatus that provides a locking stabilizer to reduce the risk of inadvertent displacement of an indwelling catheter and to do so without directly contacting the con-tacting the wound through which the catheter extends. The apparatus may feature a locking stabilizer for inhibiting movement of an indwelling catheter. Such a stabilizer includes an actuator having an actuator opening for receiv-ing the catheter into the locking stabilizer, a base having a base opening through which the catheter exits the locking stabilizer, and a gripper between the cover and the base. The gripper is configured to exert a variable gripping force on that section of the catheter that extends between the base and the cover. The actuator is operable to cause the grip to transition between exerting the gripping force and releasing the gripping force.

Embodiments include those in which the gripper includes filaments that extend between the actuator and the base. In such embodiments, each of the filaments forms an angle relative to the actuator. This angle transitions between a first value, in which the gripper exerts the gripping force on the catheter, and a second value, in which the gripper releases the gripping force from the catheter. For example, the gripper comprises filaments extend between the actuator and the base, and rotation of the actuator changes an angle, where the angle is defined between each filament and said actuator.

Further embodiments include those in which the gripper is configured to be twisted by the actuator so as to exert the gripping force on the catheter and to be untwisted by the actuator to release the gripping force from the catheter.

In still other embodiments, the gripper includes filaments that extend between the actuator and the base. In these embodiments, each filament transitions between extending along a helical path for gripping the catheter and extending along a straight path for releasing the catheter.

Also among the embodiments are those in which the gripper extends along a long path to exert the gripping force on the catheter and a short path, which is shorter than the long path (i.e., the long path is longer than the short path), to release the gripping force from the catheter.

Since catheters come in different sizes, it is useful to also have embodiments in which the actuator opening is one of several actuator openings of different sizes, each of which corresponds to a different size of catheter.

In some embodiments, the actuator is transparent to light.

In other embodiments, the locking stabilizer further includes a lock that causes the gripping force to be main-tained on the catheter. Among these are embodiments in which the lock includes a gear and a lock ring, in which case the actuator is coupled to the gear to engage the lock ring and the extent to which one rotates the gear controls a gripping force on the catheter. Also among these are those embodi-ments in which the locking stabilizer further includes a lock ring having a latch. In these embodiments, exerting a force on the latch causes the gripper to release the catheter.

Still other embodiments include those in which base includes an adhesive layer and a release layer that, when peeled off, exposes the adhesive layer, thereby enabling the locking stabilizer to adhere to a skin barrier that isolates the locking stabilizer from direct skin contact with a patient who receives the catheter.

Yet other embodiments include, in addition to the locking device itself, a skin barrier through which the catheter extends. The skin barrier includes an inner face that faces skin of a patient and an outer face that faces away from the skin. The locking stabilizer is disposed on the outer face of the skin barrier. Examples of suitable skin barriers include wound dressings and bags, such as ostomy bags.

In another aspect, the invention includes placing a locking stabilizer on a skin barrier that is disposed over an entry point into a patient, inserting the catheter through the locking stabilizer and into the entry point, and causing the locking stabilizer to exert a radially inward force to secure the catheter.

In some practices, causing the locking stabilizer to exert the radially inward force includes causing torsion in a gripper that surrounds a portion of the catheter that is within the locking stabilizer.

In other practices, causing the locking stabilizer to exert the radially inward force includes twisting an actuator on the locking stabilizer, wherein twisting the actuator causes the locking stabilizer to exert a radially inward force that secures a section of the catheter that is within the locking stabilizer.

In some cases, the catheter has a first size, and the locking stabilizer is configured to accommodate a catheter that has second size that differs from the first size. Such practices include an additional step of causing the locking stabilizer to discontinue accommodating a catheter of the second size and to begin accommodating a catheter of the first size.

Other practices those in which placing the locking stabi-lizer on the skin barrier includes placing the locking stabi-lizer on the skin barrier and either clipping the locking stabilizer to the skin barrier, such as clipping the locking stabilizer to an ostomy bag and those in which placing the locking stabilizer on the skin barrier includes causing the locking stabilizer to stick to the skin barrier, for example by peeling a release layer to expose an adhesive and using the adhesive to stick the locking stabilizer and a skin barrier, such as a dressing, together.

A number of embodiments of the invention have been described. Nevertheless, it is to be understood that the foregoing description is intended to illustrate and not to limit the scope of the invention, which is defined by the scope of the following claims. Accordingly, other embodiments are also within the scope of the following claims. For example, various modifications may be made without departing from the scope of the invention. Additionally, some of the steps described above may be order independent, and thus can be performed in an order different from that described.

Having described the invention and a preferred embodi-ment thereof, what is claimed as new and secured by letters patent is:

1. An apparatus comprising a locking stabilizer for inhib-iting movement of an indwelling catheter, said stabilizer comprising:

an actuator having an actuator opening for receiving said catheter into said locking stabilizer, a base having a base opening through which said catheter exits said locking stabilizer, and a gripper between a cover and said base, said gripper being configured to exert a variable gripping force on a section of said catheter, said section extending between said base and said cover, wherein the actuator is operable to cause said gripper to transition between exerting said gripping force and releasing said gripping force, wherein said gripper comprises filaments that extend between said actuator and said base, wherein rotation of said actuator changes an angle, wherein the angle is defined between each filament and said actuator, the angle changing between a first value, in which said gripper exerts said gripping force on said catheter, and a second value, in which said gripper releases said gripping force from said catheter.

2. The apparatus of claim 1, wherein said gripper is configured to be twisted by said actuator so as to exert said gripping force on said catheter and to be untwisted by said actuator to release said gripping force from said catheter.

3. The apparatus of claim 1, wherein each filament transitions between extending along a helical path for gripping said catheter and extending along a straight path for releasing said catheter.

4. The apparatus of claim 1, wherein said gripper extends along a long path to exert said gripping force on said catheter and a short path to release said gripping force from said catheter, wherein said long path is longer than said short path.

5. The apparatus of claim 1, wherein said actuator opening is one of a plurality of actuator openings and wherein said actuator openings have different sizes corresponding to different sizes of said catheter.

6. The apparatus of claim 1, wherein said actuator is transparent to light.

7. The apparatus of claim 1, wherein said locking stabilizer further comprises a lock that causes said gripping force to be maintained on said catheter.

8. The apparatus of claim 1, wherein said locking stabilizer further comprises a gear and a lock ring, wherein said actuator is coupled to said gear to engage said lock ring and wherein an extent to which said gear is rotated controls a gripping force on said catheter.

9. The apparatus of claim 1, wherein said locking stabilizer further comprises a lock ring having a latch and wherein exerting a force on said latch causes said gripper to release said catheter.

10. The apparatus of claim 1, wherein said base comprises an adhesive layer and a release layer that, when peeled off, exposes said adhesive layer, thereby enabling said locking stabilizer to adhere to a skin barrier that isolates said locking stabilizer from direct skin contact with a patient who receives said catheter.

11. The apparatus of claim 1, further comprising a skin barrier through which said catheter extends, wherein said skin barrier comprises an inner face that faces skin of a patient and an outer face that faces away from said skin and wherein said locking stabilizer is disposed on said outer face of said skin barrier.

12. The apparatus of claim 1, further comprising a wound dressing, wherein said wound dressing includes an inner face that faces a wound in a patient and an outer face that faces away from said wound and wherein said locking stabilizer is disposed on said outer face of wound dressing.

13. The apparatus of claim 1, wherein a patient comprises skin and wherein said apparatus further comprises a bag and a flange, wherein said bag has an inner face that faces said skin and an outer face that faces away from said skin and wherein said flange extends through said outer face and engages said locking stabilizer.

14. The apparatus of claim 1, further comprising a threaded flange that engages said locking stabilizer.

15. The apparatus of claim 1, further comprising a skin barrier through which said catheter extends and a flange that extends through a face of said skin barrier, wherein said locking stabilizer clips onto said flange.

* * * * *